United States Patent
Nishii

(10) Patent No.: US 9,201,024 B2
(45) Date of Patent: Dec. 1, 2015

(54) X-RAY IMAGING APPARATUS AND X-RAY IMAGING METHOD

(71) Applicant: CANON KABUSHIKI KAISHA, Tokyo (JP)

(72) Inventor: Yuichi Nishii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 189 days.

(21) Appl. No.: 13/915,853

(22) Filed: Jun. 12, 2013

(65) Prior Publication Data

US 2013/0336451 A1  Dec. 19, 2013

(30) Foreign Application Priority Data

Jun. 15, 2012 (JP) ................... 2012-135833

(51) Int. Cl.
```
G06F 3/00      (2006.01)
A61B 6/00      (2006.01)
G01N 23/04     (2006.01)
G01N 23/00     (2006.01)
```
(52) U.S. Cl.
CPC .................. *G01N 23/00* (2013.01); *A61B 6/00* (2013.01); *A61B 6/463* (2013.01); *A61B 6/563* (2013.01); *G01N 23/04* (2013.01); *G06F 3/00* (2013.01); *A61B 6/4233* (2013.01); *A61B 6/467* (2013.01); *G01N 2223/401* (2013.01)

(58) Field of Classification Search
CPC ................... G06F 19/321; G06F 2203/04805; G06F 2203/04806; G06F 3/14; G09G 2340/04; G06T 2207/10116; G06T 2219/2016; G06T 3/4053
See application file for complete search history.

(56) References Cited

U.S. PATENT DOCUMENTS

```
5,940,117    A  *  8/1999   Hassan et al. ............... 725/115
2008/0240533 A1 * 10/2008   Piron et al. ................. 382/131
2009/0103676 A1 *  4/2009   Nishii et al. .................. 378/4
```

FOREIGN PATENT DOCUMENTS

JP           2006026083 A      2/2006

* cited by examiner

*Primary Examiner* — Amir Alavi
*Assistant Examiner* — Kenny Cese
(74) *Attorney, Agent, or Firm* — Canon USA Inc. IP Division

(57) ABSTRACT

An X-ray imaging apparatus includes an image combining unit configured to sequentially combine divided and transmitted images, a mode selection unit configured to select one of a speed priority mode and a resolution priority mode, and a control unit configured to, if image enlargement is instructed before all the images are received, perform control to change a combining method used for the image combining unit depending on the mode selected by the mode selection unit.

15 Claims, 3 Drawing Sheets

X-RAY IMAGING APPARATUS AND X-RAY IMAGING METHOD

BACKGROUND OF THE INVENTION

1. Field of the Invention

The present invention relates to an X-ray imaging system that executes display of X-ray images communicated in a divided manner.

2. Description of the Related Art

Conventionally, trying to ensure more efficient and expeditious examinations by digitalizing, storing, and transmitting patients' medical image information obtained at hospitals is gaining momentum. Therefore, a digital system for outputting digital data using X-ray detectors, such as flat panel detector (FPD), instead of screen or film system so far has become commonly used in the field of normal X-ray imaging as well.

Further, in the digital system, the wireless communication is used in some cases for communications for improvement of operability or portability. In such cases, although the wireless data rate is improving, the transmission rate of wireless data is lower than that of a wired system. Furthermore, since a higher resolution of images continues to progress, a time taken after an image is captured until the image is displayed, that is, display delay tends to become significant. Further, in hospitals having no dedicated lines, the image data may be communicated using an existing network. In such a case, the transmission rate may also become lower than that in communications normally used.

From such a viewpoint, Japanese Patent Application Laid-Open No. 2006-26083 discusses a method for displaying the sampled reduced images in advance for speeding up.

However, enlargement processing at the stage of receiving sampled reduced image necessitates enlargement with digital processing for display with a magnification of not less than reduced image size. Consequently, there is a possibility that the enlargement processing is not suitable for a case where detailed diagnosis is needed.

On the other hand, there is an issue that waiting until all images have been received slows the subsequent imaging preparation, which has the negative effect on an imaging cycle time.

SUMMARY OF THE INVENTION

According to an aspect of the present invention, an X-ray imaging apparatus includes an image combining unit configured to sequentially combine divided and transmitted images, a mode selection unit configured to select one of a speed priority mode and a resolution priority mode, and a control unit configured to, if image enlargement is instructed before all the images are received, perform control to change a combining method used for the image combining unit depending on the mode selected by the mode selection unit.

Further features of the present invention will become apparent from the following description of exemplary embodiments with reference to the attached drawings.

DESCRIPTION OF THE EMBODIMENTS

Hereinbelow, exemplary embodiments of the present invention will be described with reference to the drawings.

Figure 1:
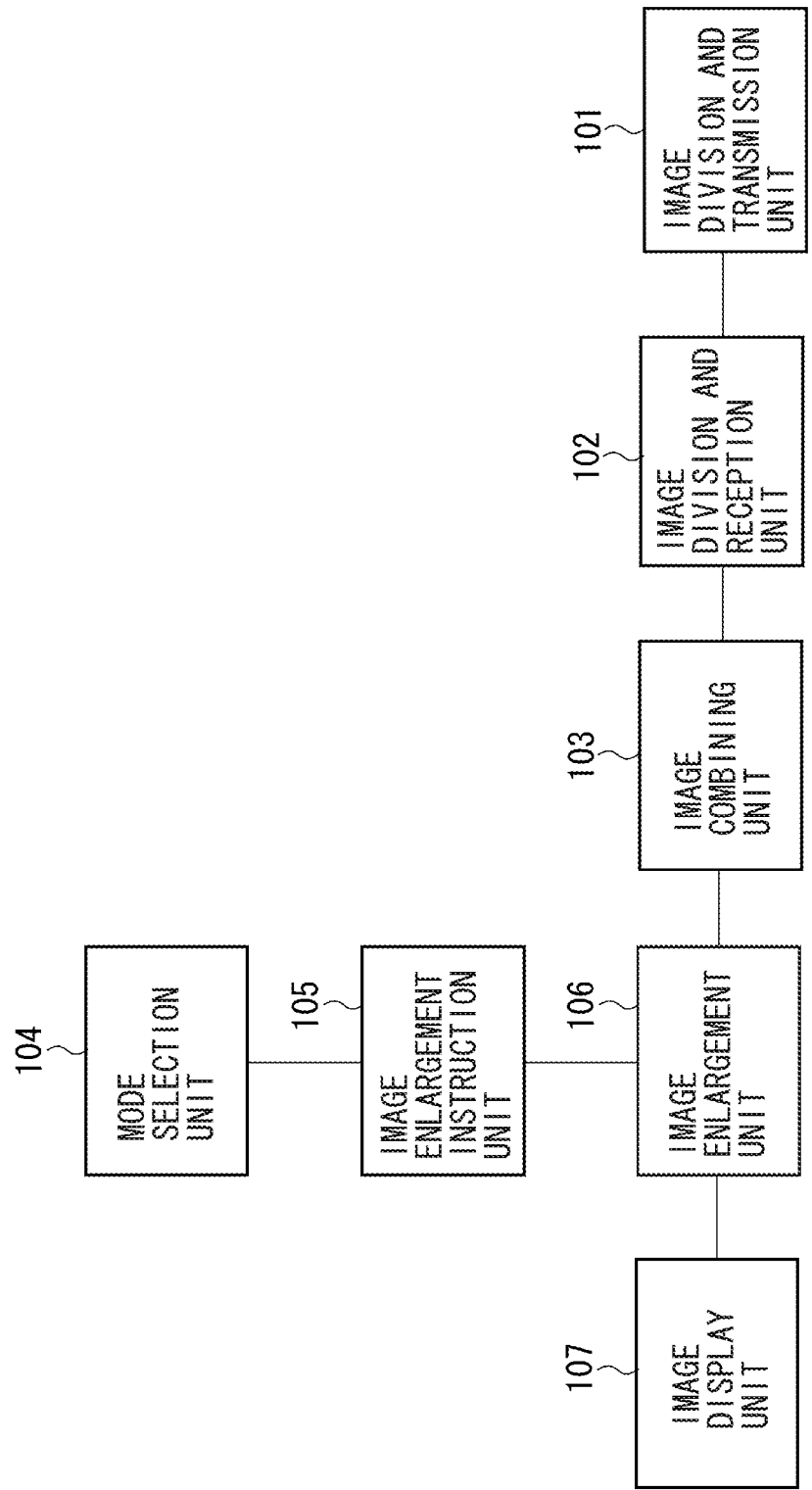
FIG. 1 illustrates a configuration diagram of an X-ray imaging system.

FIG. 1 is a block diagram illustrating a configuration of an X-ray imaging system according to a first exemplary embodiment.

The X-ray imaging system includes an image division and transmission unit 101 that divides an X-ray captured image and transmits it from an X-ray imaging apparatus. Further, the X-ray imaging system includes an image division and reception unit 102 and an image combining unit 103 that constitute a portion of a combining unit 130 (not illustrated). The image division and reception unit 102 receives transmitted images, and the image combining unit 103 performs processing for sequentially combining the images received by the image division and reception unit 102.

A mode selection unit 104 selects a speed priority mode or a resolution priority mode.

An image enlargement instruction unit 105 instructs enlargement of an image. Then, an image enlargement unit 106 constitutes the combining unit 130, and has a function of performing enlargement processing of the combined image. An image display unit 107 displays the image enlarged by the image enlargement unit 106.

The functions of respective constituent units of the X-ray imaging system are controlled by a central processing unit (CPU) (not illustrated) as a control unit 140.

A mode selected by the mode selection unit 104 is set based on information of an imaging target region or the like for each imaging operation. Since still images of chest region or the like attach greater importance on observation of fine blood vessels or bronchi than speed, the resolution priority mode is selected. On the other hand, since catheter imaging or the like requires a position of a catheter to be instantly checked, the speed priority mode is selected. The modes are stored, in association with information of imaging target regions, in a storage unit 150 (not illustrated), and the mode is selected according to the imaging information acquired from the X-ray imaging apparatus. In this manner, the mode is set in the processing of the entire system. Further, the mode may also be set for each imaging by a manual instruction of a radiographer via the mode selection unit 104.

Figure 2:
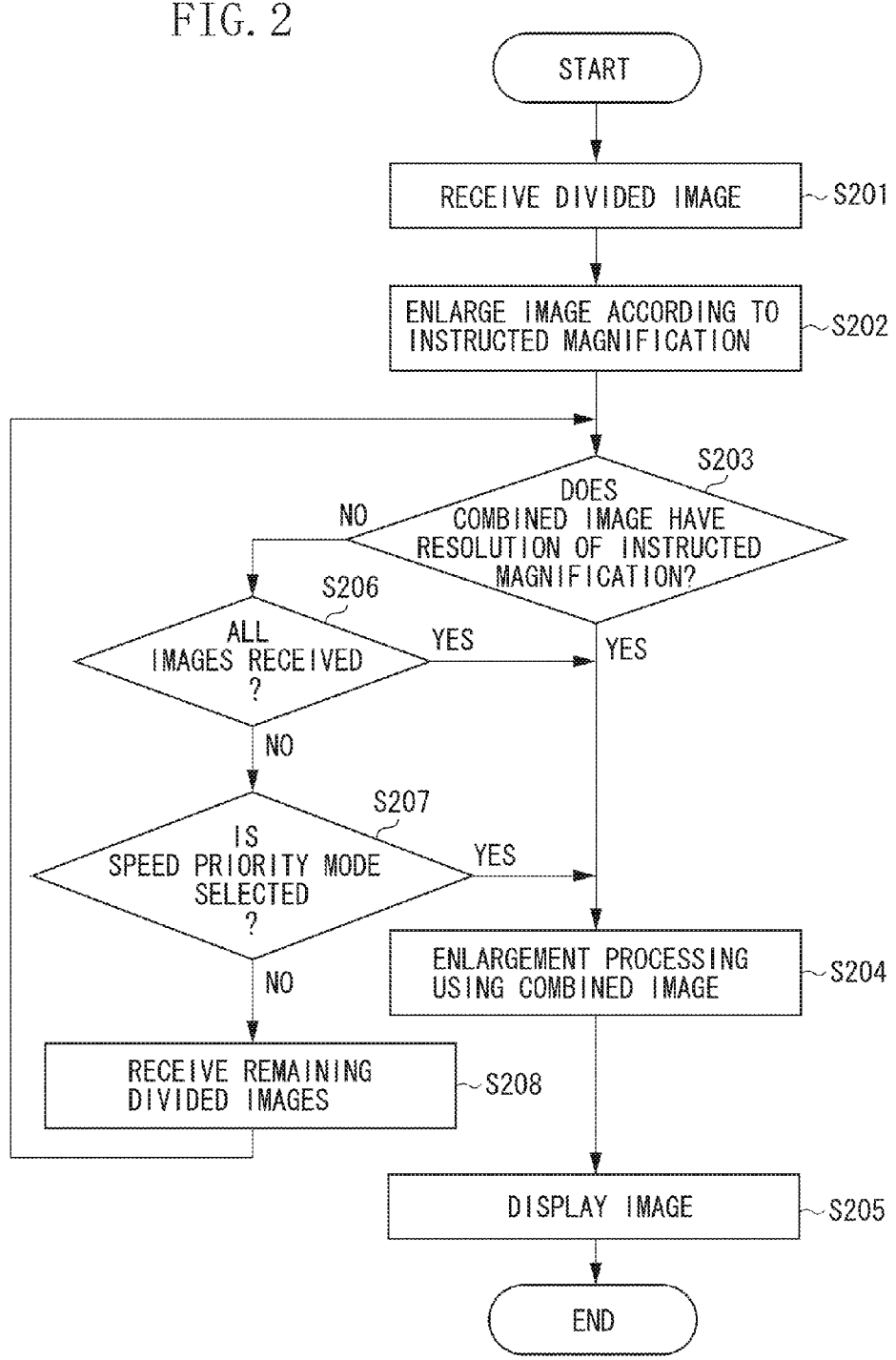
FIG. 2 illustrates a flow of processing of a first exemplary embodiment of the present invention.

An example of the processing of the present exemplary embodiment will be described in accordance with the flow in FIG. 2.

An X-ray imaging operation is executed, and an image is divided by and transmitted from the image division and transmission unit 101 of the X-ray imaging apparatus. In step S201, the image division and reception unit 102 receives the divided image. Descriptions will be provided taking an example where an image with an image size of, e.g., an image of 2048×2048 pixels is divided into four equal parts and transferred (an image of 512×512 pixels is transferred four times), and where there is a display area of 512×512 pixels.

The transfer of the divided images that are divided into the four equal parts of 512×512 pixels proceeds in parallel. In a case where enlargement instruction at a certain magnification is executed by the image enlargement instruction unit 105 in the middle of the transfer, in step S202, the control unit 140 enlarges an image for which a processing method of the combining unit 130 is changed according to the selected mode.

If the combined image, which has been combined by the combining unit 130, already has a resolution at magnification instructed for the image enlargement (YES in step S203), then in step S204, the image enlargement unit 106 performs enlargement processing using the combined image as it is. Then in step S205, the image display unit 107 displays the image.

If the combined image does not have the resolution at the magnification instructed for image enlargement (NO in step S203), and, if all images have been already received (YES in step S206), then in step S204, the image enlargement unit 106 performs enlargement processing with digital enlargement using the combined image. Then, in step S205, the image display unit 107 displays the image.

If there is an enlargement instruction of 1.5 times after having received the next 512×512 image, the combined image has a resolution at the magnification instructed for image enlargement. Therefore, in step S204, the image enlargement unit 106 executes enlargement processing using the combined image of 1024×1024 pixels generated by combining two frames of 512×512 pixels, and generates an image of 768×768 pixels, which is an image of 1.5 times of 512×512 pixels. Then in step S205, the image display unit 107 performs image display.

On the other hand, if all images have not yet been received (NO in step S206), and, if the speed priority mode is selected by the mode selection unit (YES in step S207), then in step S204, the image enlargement unit 106 performs enlargement processing with digital enlargement using the combined image of the current resolution. Then, in step S205, the image display unit 107 displays the image. Accordingly, influence to speed such as imaging cycle can be prevented from being exerted by waiting for further receptions.

If the resolution priority mode is selected by the mode selection unit 104 (NO in step S207), then in step S208, the remaining divided images are to be received until the combined image already has a resolution at the magnification instructed for image enlargement in step S203, or all images are received in step S206. For example, in the case of the resolution priority, it is assumed that an image with an image size of 2048×2048 pixels is divided into four equal parts and transferred (an image of 512×512 pixels is transferred four times), and there is a display area of 512×512 pixels. In that case, the first image of 512×512 pixels can be displayed. If there is an enlargement instruction of 1.5 times at this time point, the combined image does not have a resolution at the magnification instructed for image enlargement, and the processing proceeds to further divided reception in step S208.

By creating such a sequence, enlargement processing can be switched depending on the speed priority and resolution priority. In the case of the speed priority, reduction in imaging cycle can be prevented, and, in the case of the resolution priority, image with a high resolution can be displayed.

In the case of the speed priority, it is assumed that an image with an image size of 2048×2048 pixels is divided into four equal parts and transferred (an image of 512×512 pixels is transferred four times), and there is a display area of 512×512 pixels. In that case, the first image of 512×512 pixels can be displayed. If there is enlargement instruction of 1.5 times at this time point, further division and reception is not executed owing to the speed priority. In step S204, enlargement processing is executed to generate an image of 768×768 pixels, which is an image of 1.5 times of 512×512 pixels, using the combined image of 512×512 pixels generated by combining one frame of 512×512 pixels. Then, in step S205, image display is performed. In other words, digital enlargement is performed.

Figure 3:
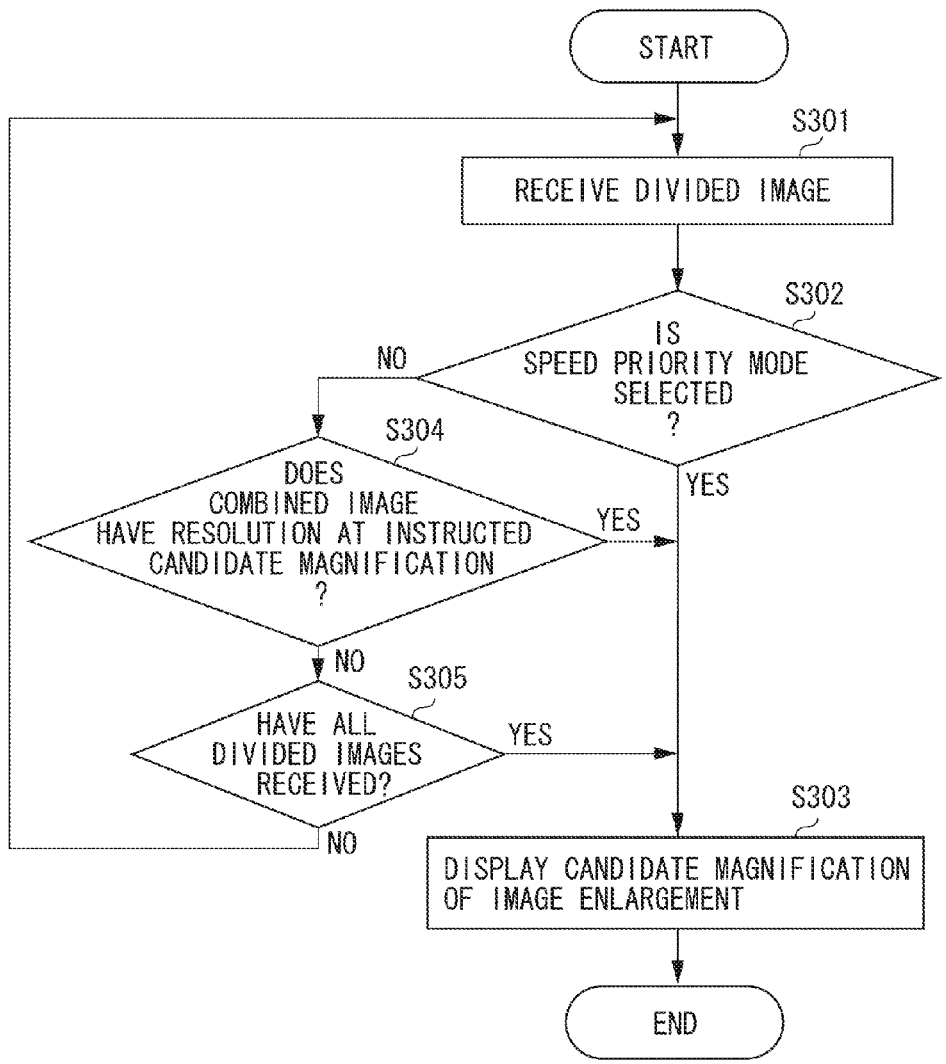
FIG. 3 illustrates a flow of processing of a second exemplary embodiment of the present invention.

Hereinbelow, the flow of processing performed by an X-ray imaging system according to a second exemplary embodiment will be described with reference to FIG. 3.

An X-ray imaging is executed, and an image is divided by and transmitted from the image division and transmission unit 101, then in step S301, the image division and reception unit 102 receives the divided images.

If the speed priority mode is selected by the mode selection unit (YES in step S302), then in step S303, the image enlargement instruction unit 105 displays a candidate magnification for enlargement instruction of an image for the purpose of performing enlargement processing with digital enlargement.

If the resolution priority mode is selected by the mode selection unit (NO in step S302), the remaining divided images are received in step S301 until the control unit 140 determines that the combined image is to have a resolution at an instructed enlargement ratio even when the image is enlarged up to the instructed image enlargement ratio in step S304, or until all images are received in step S305.

Upon determining that the combined image is to have a resolution at an instructed enlargement ratio even when the image is enlarged up to the instructed image enlargement ratio (YES in step S304), the control unit 140 permits the image display unit 107 thereon to display an image enlargement instruction portion of candidate magnification for the radiographer instructing candidates of an enlargement ratio and a resolution of the image.

If the combined image does not have the resolution (NO in step S304), and, if all images have been received (YES in step S305), then in step S303, the control unit 140 displays an image enlargement instruction portion of candidate magnification of image enlargement instruction for the purpose of performing enlargement processing with digital enlargement, since a resolution of the captured image has been the one which exceeds magnification in the first place. Further, to prohibit enlargement with digital enlargement, non-display of image enlargement instruction may be selected.

By creating such a sequence, a display method for image enlargement instruction depending on the speed priority and the resolution priority becomes switchable. In the case of the speed priority, reduction in imaging cycle can be prevented, and, in the case of the resolution priority, an image with a high resolution can be displayed.

Descriptions will be provided using a concrete example.

It is assumed that there are three types of candidate magnifications of image enlargement instructions: 2 times, 4 times, and 8 times, an image with an image size of 2048×2048 pixels is divided into four equal parts and transferred (an image of 512×512 pixels is transferred four times), and there is a display area of 512×512 pixels.

In the case of the resolution priority, the image can be displayed using the first image of 512×512 pixels, but candidate magnification of image enlargement instruction for enlargement does not have enough resolution. Therefore, when an image of 512×512 pixels is further received, an image of 1024×1024 pixels will be obtained. Since enlargement not more than two times becomes possible, an enlargement instruction portion (e.g., an enlargement button) having an option of two times is displayed. Assuming that an image of 512×512 pixels has been further received two times, that is, all images have been received, an image of 2048×2048 pixels will be obtained. Then, since enlargement of not more than four times becomes possible, the enlargement instruction portion (e.g., the enlargement button) having options of two times and four times is displayed. Regarding eight times, since the captured image does not reach resolution in the first place, the enlargement instruction portion (e.g., an enlargement button) for the purpose of digital enlargement is displayed.

In the case of the speed priority, since further reception of the divided images is not executed, the processing immediately proceeds to display of image enlargement instruction unit. In a case where the above-described enlargement instruction unit is executed during division and reception, enlargement may be executed using currently displayed image, or the latest combined image which the image division and reception unit 102 has inside.

For example, in a case where enlargement is executed using the latest combined image, that is, in a case where there is an enlargement instruction of four times in a state where an image of 512×512 pixels has been received two times, an image of 2048×2048 pixels is generated and the image is displayed by digitally enlarging the combined image of 1024×1024 pixels. In a case where enlargement is executed on currently displayed image, in the above case, an image of 2048×2048 pixels is generated and the image is displayed by digitally enlarging the currently displayed image of 512×512 pixels.

In this manner, in the case where enlargement is executed on the currently displayed image, enlargement is always executed with digital enlargement of displayed image, and, therefore, there is no unit for raising the resolution. Therefore, there may be separately provided a unit for raising a resolution.

For example, in the above-described example, an image of 2048×2048 pixels is generated and the image is displayed by digitally enlarging the currently displayed image of 512×512 pixels. However, if in a state where an image of 512×512 pixels has been already received two times by executing resolution elevation instruction, it is also possible to generate an image of 2048×2048 pixels and display the image by digitally enlarging the combined image of 1024×1024 pixels.

Hereinbelow, a third exemplary embodiment will be described. It is also possible to switch between mode selections, which have been described in the first and second exemplary embodiments, depending on operation method settings of the system.

For example, in the case of medical examination operation setting, speed of imaging cycle time is required, and, therefore, the speed priority is selected. In the case of general hospital operation setting, fine image quality is required, and, therefore, the resolution priority is selected.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135833 filed Jun. 15, 2012, which is hereby incorporated by reference herein in its entirety.

What is claimed is:

1. An X-ray imaging system comprising:
   a reception unit configured to sequentially receive data of an X-ray image;
   an image combining unit configured to acquire an image by sequentially combining the received data in response to sequential reception of the data by the reception unit;
   a mode selection unit configured to select one of a first display mode and a second display mode; and
   a control unit configured to, if the first display mode is selected and image enlargement at a certain magnification is instructed and an image having a resolution corresponding to the certain magnification is not acquired by the image combining unit, perform control to digitally enlarge the image acquired by the image combining unit, and if the second display mode is selected and image enlargement at a certain magnification is instructed and an image having a resolution corresponding to the certain magnification is not acquired by the image combining unit, perform control to wait for combining processing by the image combining unit until the image having the resolution corresponding to the certain magnification is acquired.

2. The X-ray imaging system according to claim 1, wherein, in a case where the first display mode is selected and image enlargement at a certain magnification is instructed, the control unit is configured to display an image acquired by the image combining unit as an enlarged image if an image having a resolution corresponding to the certain magnification is acquired by the image combining unit, and to digitally enlarge an image acquired by the image combining unit if an image having a resolution corresponding to the certain magnification is not acquired by the image combining unit.

3. The X-ray imaging system according to claim 1, wherein the mode selection unit is configured to select a display mode among the first display mode and the second display mode for each imaging.

4. The X-ray imaging system according to claim 1, wherein the mode selection unit is configured to select a display mode according to an imaging target region of the X-ray image.

5. The X-ray imaging system according to claim 1, wherein the mode selection unit is configured to switch a display mode according to predetermined settings.

6. The X-ray imaging system according to claim 1, wherein the control unit is configured to cause a display unit to display an image acquired by digitally enlarging an image.

7. The X-ray imaging system according to claim 1, wherein the control unit is configured to, in a case where an enlarged image acquired by digitally enlarging a first image acquired by the image combining unit at first timing is displayed by the display unit and a second image having a resolution higher than a resolution of the first image is acquired by the image combining unit at second timing later than the first timing, perform control to acquire an image corresponding to the enlarged image based on the second image.

8. An X-ray imaging system comprising:
- a reception unit configured to sequentially receive data of an X-ray image;
- an image combining unit configured to acquire an image by sequentially combine the sequentially received data;
- a mode selection unit configured to select one of a first display mode and a second display mode; and
- a control unit configured to, in a case where the first display mode is selected and image enlargement at a certain magnification is instructed, perform control to display an image acquired by the image combining unit as an enlarged image if an image having a resolution corresponding to the certain magnification is acquired by the image combining unit, and perform control to digitally enlarge an image acquired by the image combining unit if an image having a resolution corresponding to the certain magnification is not acquired by the image combining unit, and in a case where the second display mode is selected, perform control to limit a magnification specifiable in image enlargement according to a resolution of the image acquired by the image combining unit.

9. The X-ray imaging system according to claim 8, wherein the control unit is configured to control the display unit not to display a button for specifying a magnification exceeding the resolution of the image acquired by the image combining unit.

10. The X-ray imaging system according to claim 8, wherein the control unit is configured to perform control to digitally enlarge an image acquired by the image combining unit even if the second display mode is selected in a case where a magnification exceeding the resolution of the X-ray image is specified.

11. The X-ray imaging system according to claim 8, wherein the control unit is configured to perform control to cause the display unit to display a button for giving an instruction for enlargement.

12. The X-ray imaging system according to claim 8, wherein the control unit is configured to, in a case where an enlarged image acquired by digitally enlarging a first image acquired by the image combining unit at first timing is displayed by the display unit and a second image having a resolution higher than a resolution of the first image is acquired by the image combining unit at second timing later than the first timing, perform control to acquire an image corresponding to the enlarged image based on the second image.

13. The X-ray imaging system according to claim 8, wherein the control unit is configured to perform control to increase a magnification specifiable in image enlargement as a resolution of the image acquired by the image combining unit is larger.

14. A control method of controlling an X-ray imaging system, the control method comprising:
- sequentially receiving data of an X-ray image;
- acquiring an image by sequentially combining received data in response to sequential reception of the data;
- selecting one of a first display mode and a second display mode;
- performing control to digitally enlarge the acquired image if the first display mode is selected, image enlargement at a certain magnification is instructed and an image having a resolution corresponding to the certain magnification is not acquired; and
- performing control to wait for combining processing until the image having the resolution is acquired if the second display mode is selected, image enlargement at a certain magnification is instructed and an image having a resolution corresponding to the certain magnification is not acquired.

15. A control method of controlling an X-ray imaging system, the control method comprising:
- sequentially receiving data of an X-ray image;
- acquiring an image by sequentially combine the sequentially received data;
- selecting one of a first display mode and a second display mode;
- in a case where the first display mode is selected and image enlargement at a certain magnification is instructed, performing control to display an acquired image as an enlarged image if an image having a resolution corresponding to the certain magnification is acquired, and performing control to digitally enlarge an acquired image if an image having a resolution corresponding to the certain magnification is not acquired; and
- in a case where the second display mode is selected, performing control to limit a magnification specifiable in image enlargement according to a resolution of the acquired image.

* * * * *